(12) United States Patent
Aharoni et al.

(10) Patent No.: US 7,736,390 B2
(45) Date of Patent: *Jun. 15, 2010

(54) INTRAOCULAR IMPLANTS

(75) Inventors: Eli Aharoni, Rishon Le Zion (IL); Gideon Dotan, Yehud (IL); Ruti Alon, Michmoret (IL); Yossi Gross, Moshav Mazor (IL)

(73) Assignee: Visioncare Ophthalmic Technologies Inc., Saratoga, CA (US)

( * ) Notice: Subject to any disclaimer, the term of this patent is extended or adjusted under 35 U.S.C. 154(b) by 724 days.

This patent is subject to a terminal disclaimer.

(21) Appl. No.: 10/982,987

(22) Filed: Nov. 4, 2004

(65) Prior Publication Data

US 2005/0062679 A1 Mar. 24, 2005

Related U.S. Application Data

(62) Division of application No. 10/321,793, filed on Dec. 17, 2002, now Pat. No. 7,001,427.

(51) Int. Cl.
*A61F 2/16* (2006.01)
(52) U.S. Cl. ............... 623/6.13; 623/6.22; 623/6.34
(58) Field of Classification Search ........... 623/6.13, 623/6.22, 6.32, 6.34–6.37, 6.4
See application file for complete search history.

(56) References Cited

U.S. PATENT DOCUMENTS

| | | | |
|---|---|---|---|
| 3,515,461 A | 6/1970 | Rayces et al. | |
| 4,074,368 A | 2/1978 | Levy, Jr. et al. | |
| 4,056,855 A | 8/1984 | Kelman | |
| 4,463,458 A | 8/1984 | Seidner | |
| 4,527,294 A | 7/1985 | Heslin | |
| 4,581,031 A | 4/1986 | Koziol et al. | |
| 4,596,578 A | 6/1986 | Kelman | |
| 4,666,446 A | 5/1987 | Koziol et al. | |
| 4,710,197 A | 12/1987 | Donn et al. | |
| 4,731,078 A | 3/1988 | Stoy et al. | |
| 4,743,254 A | 5/1988 | Davenport | |
| 4,833,890 A | 5/1989 | Kelman | |
| 4,892,543 A | 1/1990 | Turley | |
| 4,911,714 A | 3/1990 | Poley | |
| 4,911,715 A | 3/1990 | Kelman | |
| 5,016,633 A | 5/1991 | Chow | |
| 5,026,396 A | 6/1991 | Darin | |
| 5,044,743 A | 9/1991 | Ting | |

(Continued)

FOREIGN PATENT DOCUMENTS

DE 34 28 895 A1 2/1986

(Continued)

OTHER PUBLICATIONS

An Office Action dated Jan. 31, 2009, which issued during the prosecution of Applicant's U.S. Appl. No. 11/420,327.

(Continued)

*Primary Examiner*—David H. Willse
(74) *Attorney, Agent, or Firm*—Fish & Richardson P.C.

(57) ABSTRACT

An artificial vision system including a sealed capsule adapted for intraocular placement upstream of a retina, an electronic display located within the sealed capsule and focusing optics located within the sealed capsule and arranged for focusing an image on the electronic display onto the retina.

9 Claims, 11 Drawing Sheets

U.S. PATENT DOCUMENTS

| | | | |
|---|---|---|---|
| 5,108,429 A * | 4/1992 | Wiley | 623/6.22 |
| 5,354,335 A | 10/1994 | Lipshitz et al. | |
| 5,397,350 A | 3/1995 | Chow et al. | |
| 5,405,387 A | 4/1995 | Sodero et al. | |
| 5,964,802 A * | 10/1999 | Anello et al. | 623/6.4 |
| 6,197,057 B1 | 3/2001 | Peyman et al. | |
| 6,358,280 B1 | 3/2002 | Herrick | |
| 6,400,989 B1 | 6/2002 | Eckmiller | |
| 6,529,752 B2 | 3/2003 | Krausman et al. | |
| 6,638,304 B2 * | 10/2003 | Azar | 623/6.22 |
| 6,847,847 B2 | 1/2005 | Nisch et al. | |
| 6,849,090 B2 | 2/2005 | Nigam | |
| 6,902,577 B2 | 6/2005 | Lipshitz et al. | |
| 6,913,620 B2 | 7/2005 | Lipshitz et al. | |
| 7,001,427 B2 | 2/2006 | Aharoni | |
| 7,008,448 B2 | 3/2006 | Lipshitz et al. | |
| 7,079,900 B2 | 7/2006 | Greenburg et al. | |
| 7,160,252 B2 | 1/2007 | Cho et al. | |
| 7,276,080 B2 | 10/2007 | Murakami et al. | |
| 2002/0143395 A1 | 10/2002 | Skottun | |
| 2002/0173846 A1 | 11/2002 | Blake et al. | |
| 2003/0060881 A1 | 3/2003 | Glick et al. | |
| 2003/0078656 A1 | 4/2003 | Nguyen | |
| 2003/0105522 A1 | 6/2003 | Glazier | |
| 2003/0187502 A1 | 10/2003 | Lipshitz | |
| 2003/0187503 A1 | 10/2003 | Lipshitz et al. | |
| 2004/0117011 A1 | 6/2004 | Aharoni et al. | |
| 2004/0148022 A1 | 7/2004 | Eggleston | |
| 2004/0236421 A1 | 11/2004 | Lipshitz et al. | |
| 2005/0065602 A1 | 3/2005 | Aharoni et al. | |
| 2005/0071002 A1 | 3/2005 | Glazier | |
| 2005/0090875 A1 | 4/2005 | Palanker et al. | |
| 2005/0154457 A1 | 7/2005 | Aharoni et al. | |
| 2005/0222860 A1 | 10/2005 | Kawaoka et al. | |

FOREIGN PATENT DOCUMENTS

| | | |
|---|---|---|
| DE | 19501444 A1 | 7/1996 |
| EP | 0 099 641 | 2/1984 |
| EP | 0 162 573 A2 * | 11/1985 |
| EP | 242043 | 10/1987 |
| EP | 1438930 | 7/2004 |
| EP | 1475055 | 11/2004 |
| FR | 2713082 | 6/1995 |
| GB | 877083 | 9/1961 |
| WO | WO 88/06430 | 9/1988 |
| WO | WO-0004849 | 2/2000 |

OTHER PUBLICATIONS

An Office Action dated Jan. 20, 2009, which issued during the prosecution of Applicant's Japanese Patent Application No. 2004-7118.

An International Search Report dated Feb. 26, 2007, which issued during the prosecution of Applicant's PCT Patent Application No. PCT/IL06/00873.

An Office Action dated Aug. 29, 2009, which issued during prosecution of Applicant's Canadian Patent Application No. 2,455,076.

An Office Action dated Sep. 8, 2009, which issued during the prosecution of Applicant's Japanese Patent Application No. 2004-560169.

An Office Action dated Sep. 9, 2009, which issued during the prosecution of Applicant's U.S. Appl. No. 11/069,581.

Office Action mailed Dec. 8, 2009 during prosecution of corresponding U.S. Appl. No. 10/489,388.

* cited by examiner

INTRAOCULAR IMPLANTS

FIELD OF THE INVENTION

The present invention relates to ocular implants generally and more particularly to intraocular implants and techniques for implanting thereof.

BACKGROUND OF THE INVENTION

The following U.S. patents of the present inventor are believed to represent the current state of the art:

U.S. Pat. Nos. 5,814,103; 5,876,442; 5,928,283; 6,007,579 and 6,066,171.

SUMMARY OF THE INVENTION

The present invention seeks to provide an artificial vision system.

There is thus provided in accordance with a preferred embodiment of the present invention an artificial vision system including a sealed capsule adapted for intraocular placement upstream of a retina, an electronic display located within the sealed capsule and focusing optics located within the sealed capsule and arranged for focusing an image on the electronic display onto the retina.

In accordance with another preferred embodiment of the present invention the electronic display includes an LCD display.

In accordance with yet another preferred embodiment of the present invention the artificial vision system also includes electronic circuitry located within the sealed capsule for operating the electronic display, the electronic circuitry being located outside an optical path defined between the electronic display and the focusing optics. Additionally, the electronic circuitry includes a wireless data receiver operative to receive image data for display on the electronic display. Alternatively, the electronic circuitry includes a wireless energy receiver for wirelessly receiving electrical energy for operating the electronic display.

In accordance with still another preferred embodiment the artificial vision system also includes wireless image transmission functionality operative to transmit the image data to the wireless data receiver. Preferably, the wireless image transmission functionality includes at least one of RF and IR image transmission functionality.

In accordance with yet a further preferred embodiment of the present invention the electronic circuitry includes an electrical power source for providing electrical energy for operating the electronic display. Additionally, the power source for providing electrical energy for operating the electronic display is a rechargeable power source. Alternatively, the power source for providing electrical energy for operating the electronic display is a wirelessly rechargeable power source. Additionally or alternatively, the power source for providing electrical energy for operating the electronic display is rechargeable using at least one of ultrasonic, electromagnetic and photovoltaic power source.

In accordance with still another preferred embodiment of the present invention the artificial vision system also includes an image acquirer for acquiring an image to be displayed on the electronic display. Additionally, the image acquirer is mounted onto eyeglasses.

Preferably, the focusing optics includes a single lens. Alternatively, the focusing optics includes multiple lenses.

There is also provided in accordance with another preferred embodiment of the present invention a method for providing artificial vision including implanting a sealed capsule in a user's eye upstream of a retina, the sealed capsule incorporating an electronic display and focusing optics for focusing an image on the electronic display onto the retina, acquiring image data and transmitting the image data to the electronic display for display thereon.

Preferably, the transmitting includes wireless transmission to electronic circuitry located within the sealed capsule for operating the electronic display.

Additionally, the method for providing artificial vision also includes wirelessly transmitting electrical energy for operating the electronic display to a location inside the capsule.

There is further provided in accordance with yet another preferred embodiment of the present invention an intraocular implant, for placement upstream of a retina, including a telescope body defining an optical path for light to pass therethrough, at least one first lens and at least one second lens enclosed in the telescope body, positioning means, for positioning at least one of the lenses along its optical axis relative to another at least one of the lenses, operative to focus objects located at multiple distances onto the retina and mounting structure connected to the telescope body for mounting the implant in an eye.

In accordance with another preferred embodiment the positioning means includes a range finder. Alternatively, the positioning means includes a focus resolver. In accordance with yet another preferred embodiment of the present invention the positioning means is responsive to a user input.

In accordance with another preferred embodiment the positioning means includes a mounting for at least one of the lenses, at least one magnet and at least one electromagnetic coil, interacting with the at least one magnet.

In accordance with yet another preferred embodiment the positioning means is responsive to an input from an input device external to the telescope body.

There is further provided in accordance with still another preferred embodiment of the present invention an intraocular implant system including a sealed capsule, including at least one negative lens and at least one air bubble, and at least one positive lens located outside the sealed capsule.

In accordance with a preferred embodiment of the present invention the at least one positive lens includes an eyeglass lens. Alternatively or additionally, the at least one positive lens includes a contact lens. Additionally or alternatively, the at least one positive lens includes a lens implanted in the anterior chamber of an eye. Additionally, the implanted lens includes an air capsule.

In accordance with another preferred embodiment, an external wall of the sealed capsule includes the at least one negative lens.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
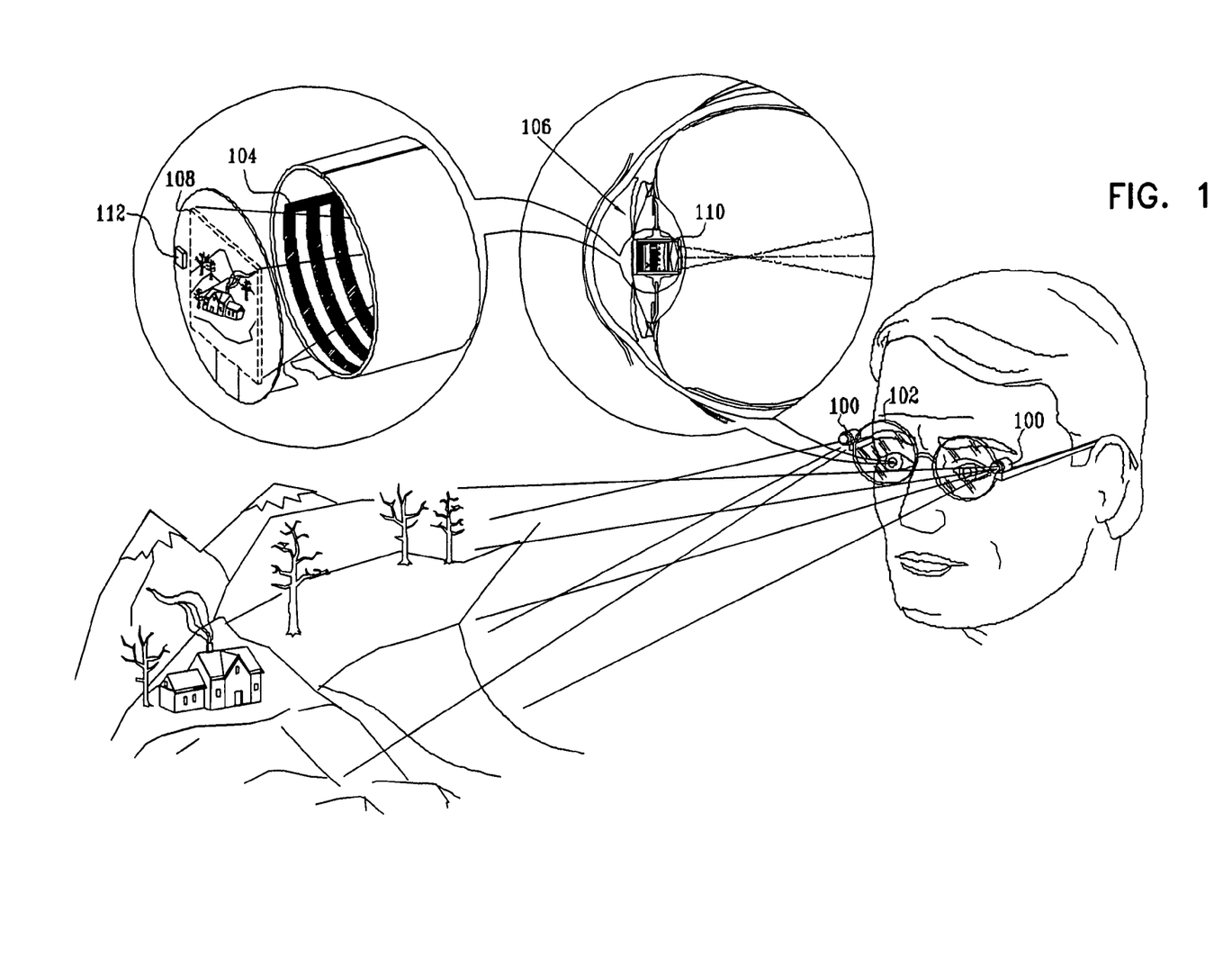
FIG. 1 is a simplified pictorial illustration of an artificial vision system constructed and operative in accordance with a preferred embodiment of the present invention.

Reference is now made to FIG. 1, which is a simplified pictorial illustration of an artificial vision system constructed and operative in accordance with a preferred embodiment of the present invention. As seen in FIG. 1, there is provided an artificial vision system including a real time imaging device, such as a CCD camera. The illustrated embodiment includes both implanted and external imaging devices for the purposes for illustration, it being understood that typically either implanted or external imaging devices will be employed, although both could be used together.

In the illustrated embodiment of FIG. 1, at least one and preferably plural external imaging devices, here designated by reference numeral 100, are typically mounted on a pair of eyeglasses 102, as shown. The external imaging devices 100 view a scene, preferably in stereo. The image information captured by the external imaging devices 100 is transmitted wirelessly, preferably by conventional IR or RF techniques, to electronic circuitry 104 located within a sealed capsule 106 adapted for intraocular placement upstream of a retina. The electronic circuitry 104 is operative to display the captured image as seen by the external imaging devices 100 in real time on an electronic display 108, such as a backlit or self-illuminated LCD display.

Focusing optics, typically in the form of a lens assembly 110, in the sealed capsule 106, are operative to image the displayed image onto the retina of a user.

Alternatively or additionally, an implanted imaging device, here designated by reference numeral 112, is located on an outer surface of or interior of each sealed capsule 106. The internal imaging devices 112 view a scene, preferably in stereo. The image information captured by the internal imaging devices 100 is transmitted in a wired or wireless manner, such as by conventional IR or RF techniques, to electronic circuitry 104 located within sealed capsule 106 adapted for intraocular placement upstream of a retina. The electronic circuitry 104 is operative to display the captured image as seen by the internal imaging devices 112 in real time on electronic display 108, such as a backlit or self-illuminated LCD display. Focusing optics, preferably lens assembly 110, in the sealed capsule 106, are operative to image the displayed image onto the retina of a user.

It is noted that the electronic circuitry 104 is located outside an optical path defined between the electronic display 108 and said focusing optics 110.

It is appreciated that, in addition to transmitting an image of a scene, external imaging devices 100 or internal imaging devices 112 may be operative to transmit any other suitable digital information, such as a video image, via electronic circuitry 104 to electronic display 108.

Figure 2:
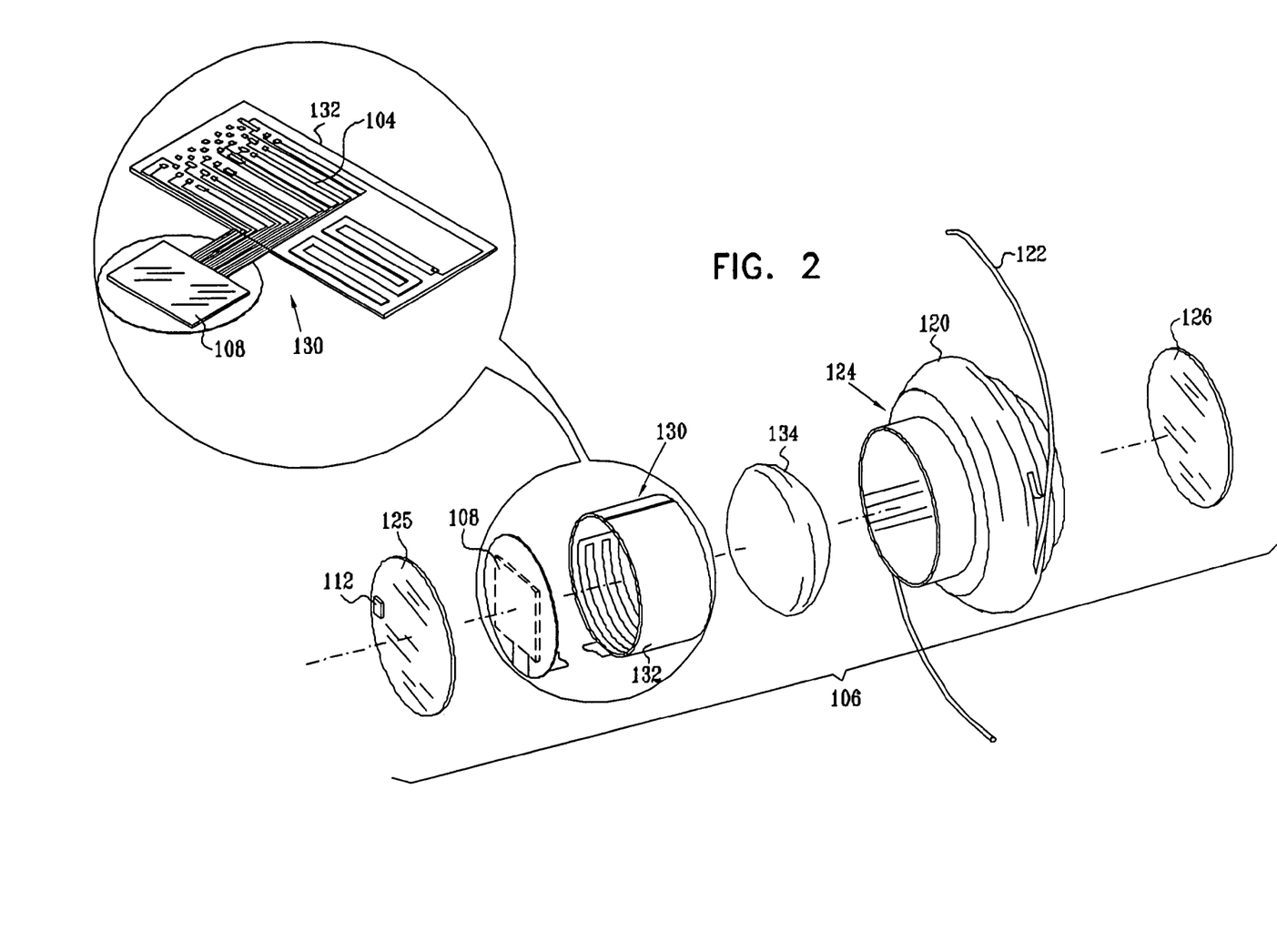
FIG. 2 is a simplified exploded view pictorial illustration of an implant forming part of the system of FIG. 1.
Figure 3:
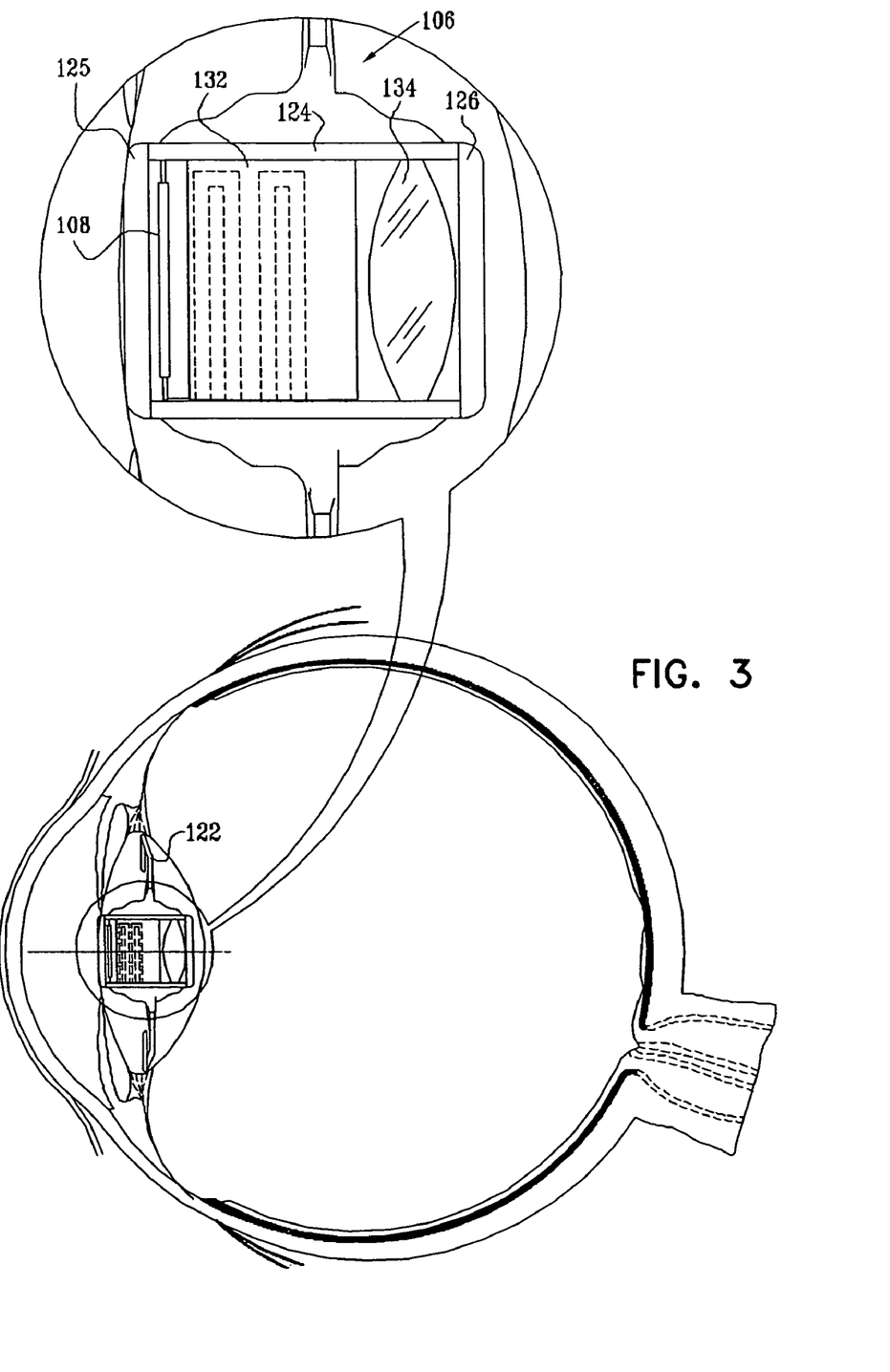
FIG. 3 is a simplified partially sectional side view illustration of the implant of FIG. 2.

Reference is now made to FIGS. 2 and 3, which illustrate some details of the implantable sealed capsule 106 which is shown implanted in a user in FIG. 1. The sealed capsule 106 is defined by an intraocular implant housing 120 having mounting haptics 122 and defining a generally cylindrical capsule body 124. Hermetically sealed to capsule body 124 are a front sealing plate 125 and a back sealing plate 126. Back sealing plate 126 is transparent. An internal imaging device 112 is shown mounted on an outside surface of front sealing plate 125. Capsules of this type are described in applicants' U.S. patent application Ser. No. 09/678,559, filed Oct. 3, 2000 and entitled "TELESCOPIC INTRAOCULAR LENS", which is a divisional application of U.S. patent application Ser. No. 09/222,330, filed Dec. 29, 1998 and entitled "TELESCOPIC INTRAOCULAR LENS", subsequently abandoned, and U.S. patent application Ser. No. 09/721,916, filed Nov. 27, 2000 and entitled "TELESCOPIC INTRAOCULAR LENS", the disclosures of which are hereby incorporated by reference.

Preferably disposed within sealed capsule 106 is an electronic circuit and display assembly, here designated by reference numeral 130. Assembly 130 preferably includes electronic display 108 (FIG. 1) which is coupled to electronic circuitry 104 (FIG. 1), preferably including a wireless receiver for image data. Display 108 is arranged to lie generally parallel to front sealing plate 125, while electronic circuitry 104 is preferably embodied on a flexible circuit board 132 which is arranged to lie in a cylindrical configuration, peripherally of the optical path between display 108 and back sealing plate 126, so as not to interfere with the optical pathway between the display 108, focusing optics 110 (FIG. 1), here shown as a lens 134, and the user's retina. It is appreciated that even though the embodiment illustrated in FIGS. 2 and 3 shows a single lens 134, focusing optics 110 may also comprise multiple lenses as shown in the embodiment of FIG. 1.

In accordance with a preferred embodiment of the present invention, the electronic circuitry 104 also includes a wireless energy receiver such as a resonant circuit (not shown) and energy storage facilities, such as a rechargeable miniature battery or capacitor (not shown) for wirelessly receiving and storing electrical energy for operating the electrical circuitry and the electronic display.

In the embodiment of FIG. 1, an electrical power source (not shown) external to a user's body, such as a battery mounted in eyeglasses 102, and a suitable energy transmitter, such as a resonant circuit, may be used to transmit operating power to electronic circuit 104 inside sealed capsule 106. Any suitable electrical power source, such as an ultrasonic, electromagnetic and photovoltaic power source, may alternatively be employed interiorly or exteriorly of the capsule.

Figures 4A, 4B:
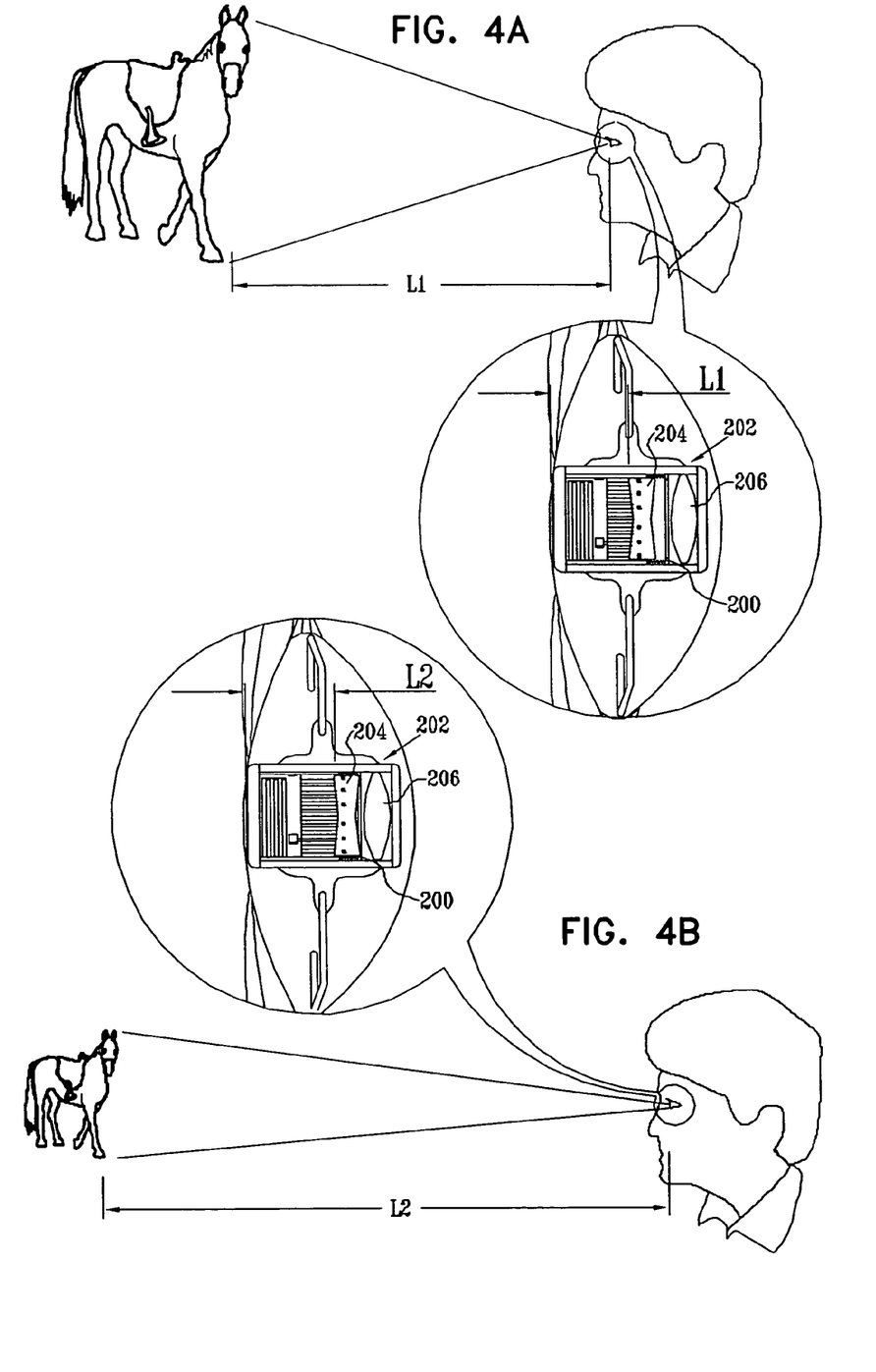
FIGS. 4A and 4B are simplified illustrations of the use of a variable focal length lens arrangement in the implant system of FIGS. 1-3.

Reference is now made to FIGS. 4A and 4B, which are simplified illustrations of the use of a variable focal length lens arrangement, usable in the implant system of FIGS. 1-3, as well as in other intraocular implant systems. As seen in FIGS. 4A and 4B, there is provided an intraocular implant system which includes variable focus optics 200 located within a sealed capsule 202 implanted within the eye of a user.

From a consideration of FIGS. 4A and 4B, it can be seen that the relative positioning of at least two lenses 204 and 206 within variable focus optics 200 is variable, preferably in response to an electrical control input, so as to correctly focus onto objects at differing distances.

The relative positioning is preferably produced by an electric displacer, such as a piezoelectric device or a rotary electric motor in response to a wirelessly received viewed object distance indicating input, which may be provided by a conventional range finder or focus resolver, such as employed in conventional automatic focus cameras. Alternatively, a user input may be provided.

Figure 5:
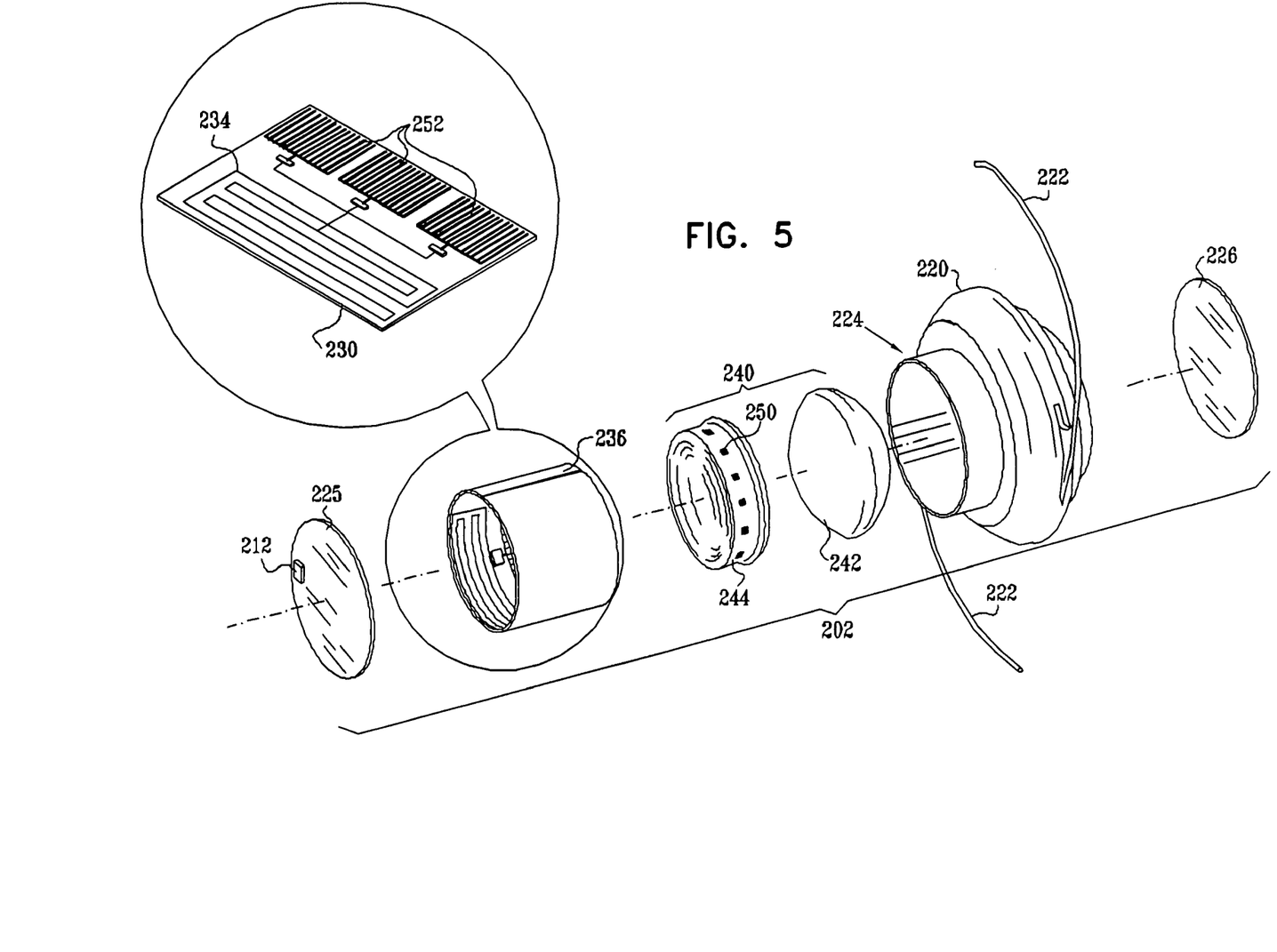
FIG. 5 is a simplified exploded view pictorial illustration of an implant forming part of the system of FIGS. 4A & 4B.
Figure 6:
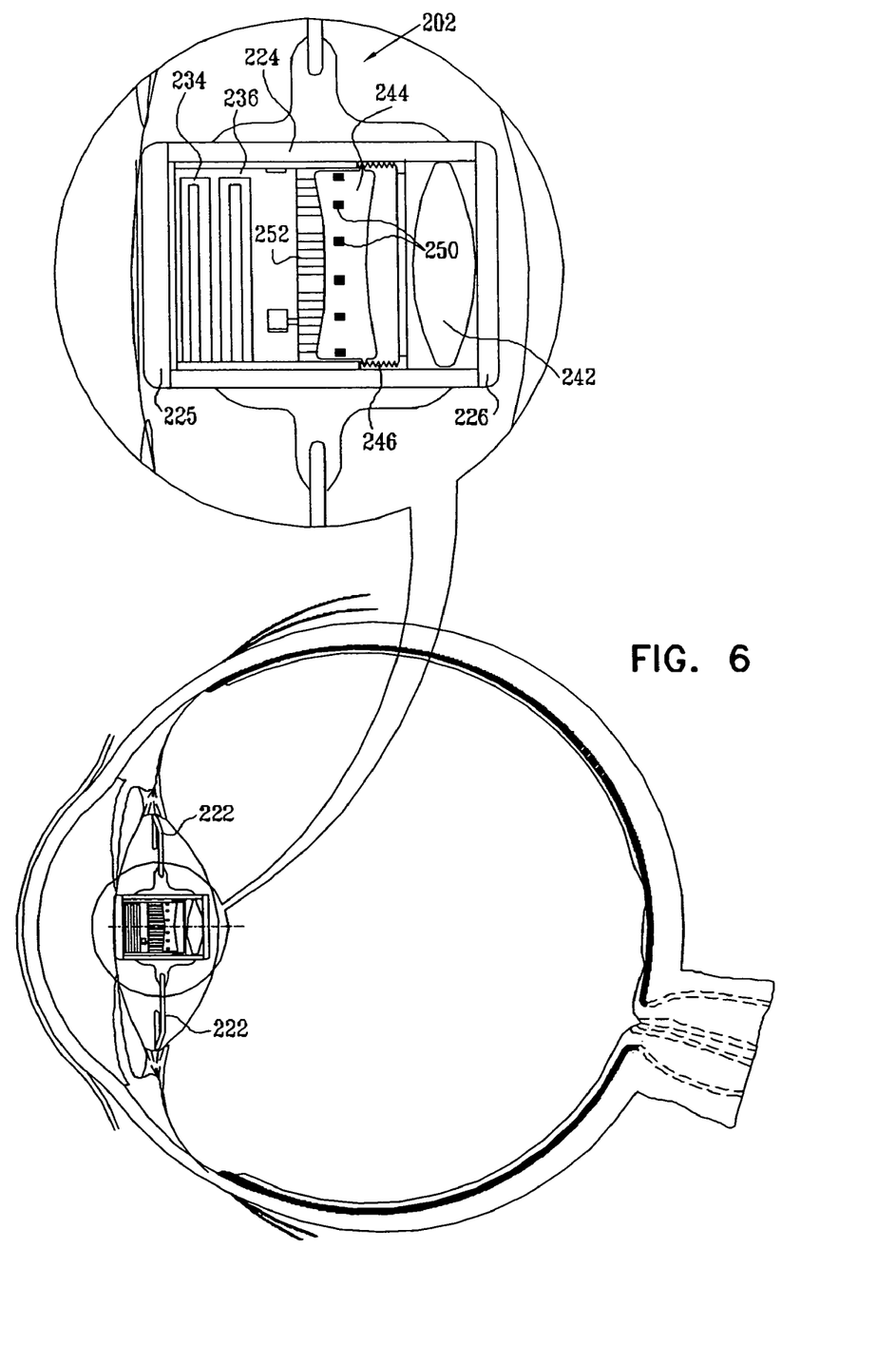
FIG. 6 is a simplified partially sectional side view illustration of the implant of FIG. 5.

Reference is now made to FIGS. 5 and 6, which illustrate some details of the implantable sealed capsule 202 shown implanted in a user in FIGS. 4A and 4B. The sealed capsule 202 is defined by an intraocular implant housing 220 having mounting haptics 222 and defining a generally cylindrical capsule body 224. Hermetically sealed to capsule body 224 are a front sealing plate 225 and a back sealing plate 226. Front sealing plate 225 and back sealing plate 226 are transparent. An internal range finding device 212 is shown mounted on an outside surface of front sealing plate 225. Capsules of this type are described in applicants' U.S. patent application Ser. No. 09/678,559, filed Oct. 3, 2000 and entitled "TELESCOPIC INTRAOCULAR LENS", which is a divisional application of U.S. patent application Ser. No. 09/222,330, filed Dec. 29, 1998 and entitled "TELESCOPIC INTRAOCULAR LENS", subsequently abandoned, and U.S. patent application Ser. No. 09/721,916, filed Nov. 27, 2000 and entitled "TELESCOPIC INTRAOCULAR LENS", the disclosures of which are hereby incorporated by reference.

An electronic circuit and focus control assembly, here designated by reference numeral 230, is preferably disposed within sealed capsule 202. Assembly 230 preferably includes electronic circuitry 234, preferably including a wireless receiver for receiving ranging information. Electronic circuitry 234 is preferably embodied on a flexible circuit board 236 which is arranged to lie in a cylindrical configuration, peripherally of the optical path through capsule 202 via back sealing plate 226, so as not to interfere with the optical pathway between the viewed scene, via variable focusing optics 240, and the user's retina.

In the illustrated embodiment, the variable focusing optics comprise a fixed lens 242 and a variable position lens 244 which is selectably positionable along its optical axis with respect to fixed lens 242, thus varying the focal length of the variable focusing optics.

In the illustrated embodiment, a threaded mounting 246 is provided for lens 244, and at least one permanent magnet 250, and at least one electromagnetic coil 252 interacting therewith, is preferably provided for selectably threading lens 244 in threaded mounting 246, thus varying its separation from lens 242, in response to control signals from electronic circuitry 234, thereby providing appropriate focusing on a distant viewed object.

It is appreciated that any other suitable mechanism for selectable mutual displacement of lenses 242 and 244 may be employed.

In accordance with a preferred embodiment of the present invention, the electronic circuitry 234 also includes a wireless energy receiver such as a resonant circuit (not shown) and energy storage facilities, such as a rechargeable miniature battery or capacitor (not shown) for wirelessly receiving and storing electrical energy for operating the electrical circuitry 234 and the electromagnetic coil 252.

In one embodiment of the invention, an electrical power source (not shown) external to a user's body, such as a battery mounted in eyeglasses, and a suitable range finder and energy transmitter, such as a resonant circuit, may be used to transmit operating power to electronic circuit 234 inside sealed capsule 202. Any suitable electrical power source, such as an ultrasonic, electromagnetic and photovoltaic power source, may alternatively be employed interiorly or exteriorly of the capsule.

It is appreciated that even though the illustrated embodiment comprises two lenses, any suitable configuration of two or more lenses may also be employed.

Reference is now made to FIGS. 7A-7G, which are simplified sectional illustrations showing examples of alternative implementations of an intraocular lens system employing a sealed capsule 300 implanted in an eye and including at least one negative lens 302 and at least one air bubble 304 and at least one positive lens located outside of the sealed capsule.

Figure 7A:
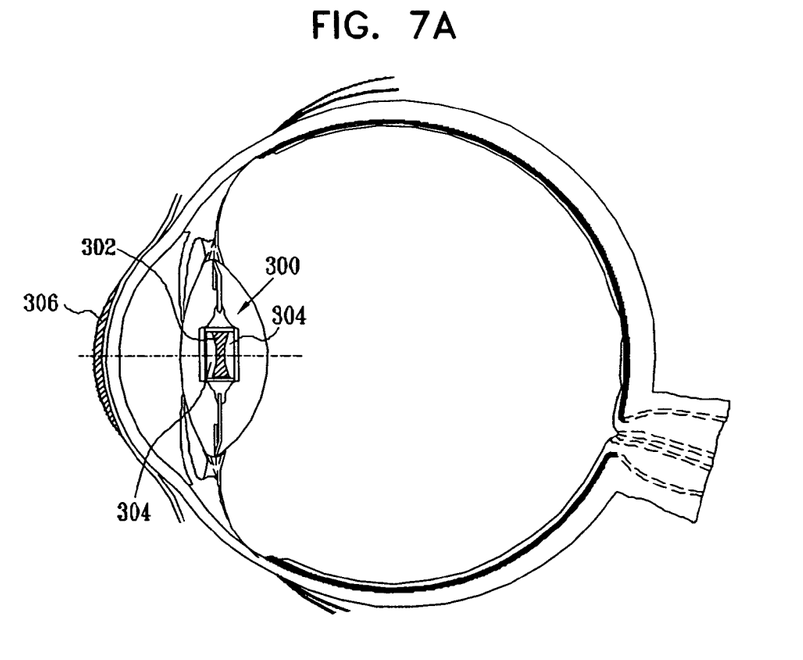
FIGS. 7A-7G are simplified sectional illustrations showing alternative implementations of an intraocular lens system employing a sealed capsule arranged for implantation in an eye and including at least one negative lens and at least one air bubble and at least one positive lens located outside of the sealed capsule.
Figure 7B:
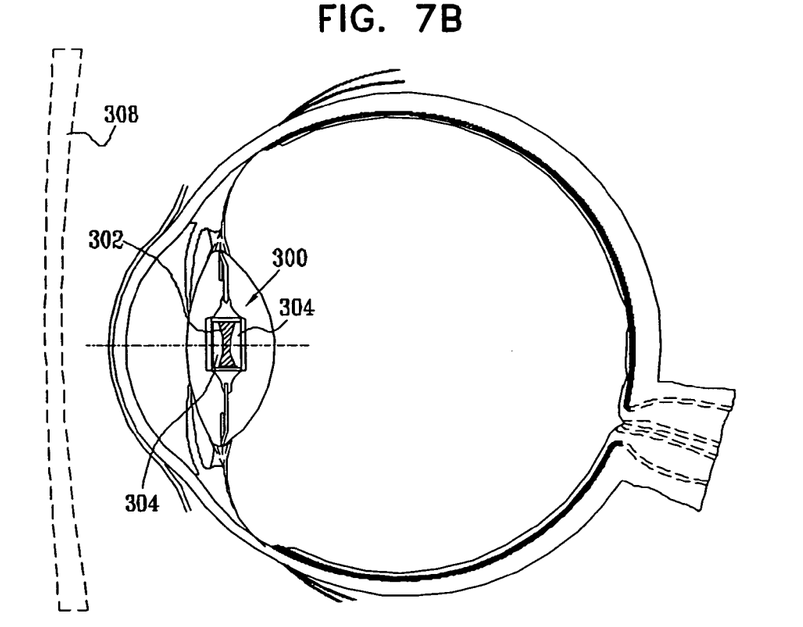
Figure 7C:
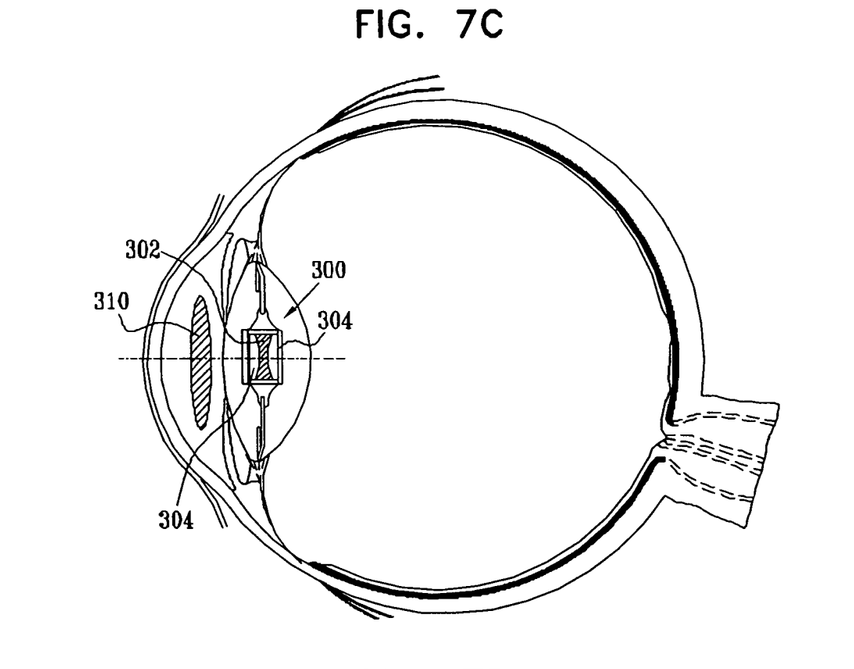

FIG. 7A shows an embodiment where the positive lens is a contact lens 306. In the embodiment of FIG. 7B, the positive lens is an eyeglass lens 308. FIG. 7C illustrates an embodiment where the positive lens is a lens 310 implanted in the anterior chamber of the eye.

Figure 7D:
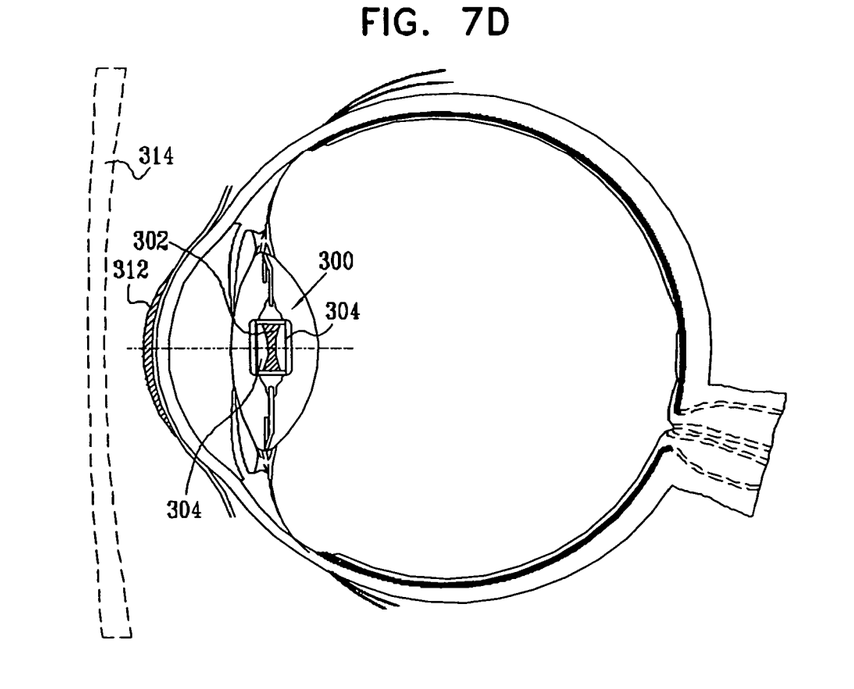
Figure 7E:
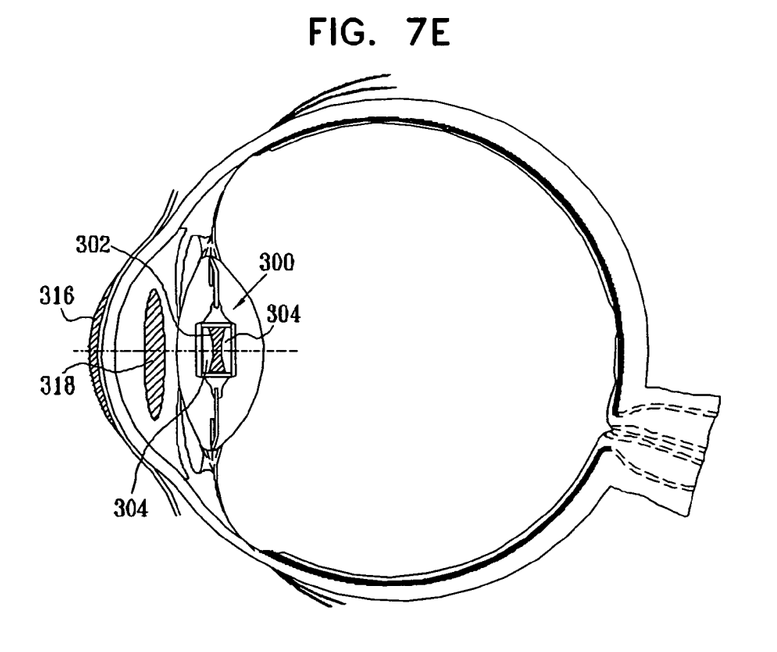
Figure 7F:
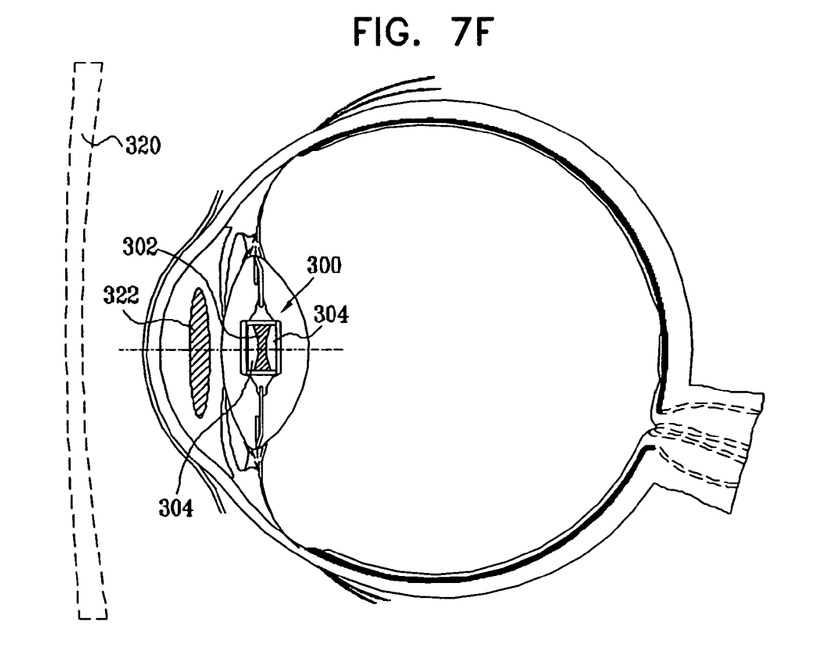

FIG. 7D shows an embodiment where two positive lenses are provided, a contact lens 312 and an eyeglass less 314. In the embodiment of FIG. 7E, two positive lenses are provided, a contact lens 316 and a lens 318 implanted in the anterior chamber of the eye. FIG. 7F illustrates an embodiment where the two positive lenses are an eyeglass lens 320 and a lens 322 implanted in the anterior chamber of the eye.

Figure 7G:
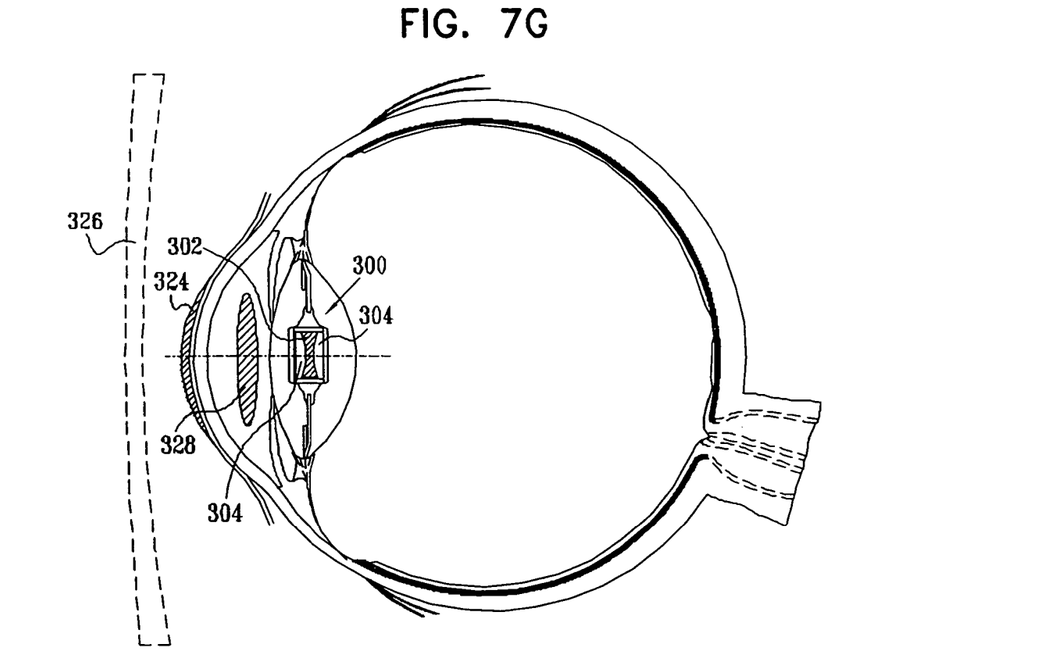

FIG. 7G shows an embodiment where three positive lenses are employed, contact lens 324, eyeglass lens 326 and a lens 328 implanted in the anterior chamber of the eye.

Figure 8:
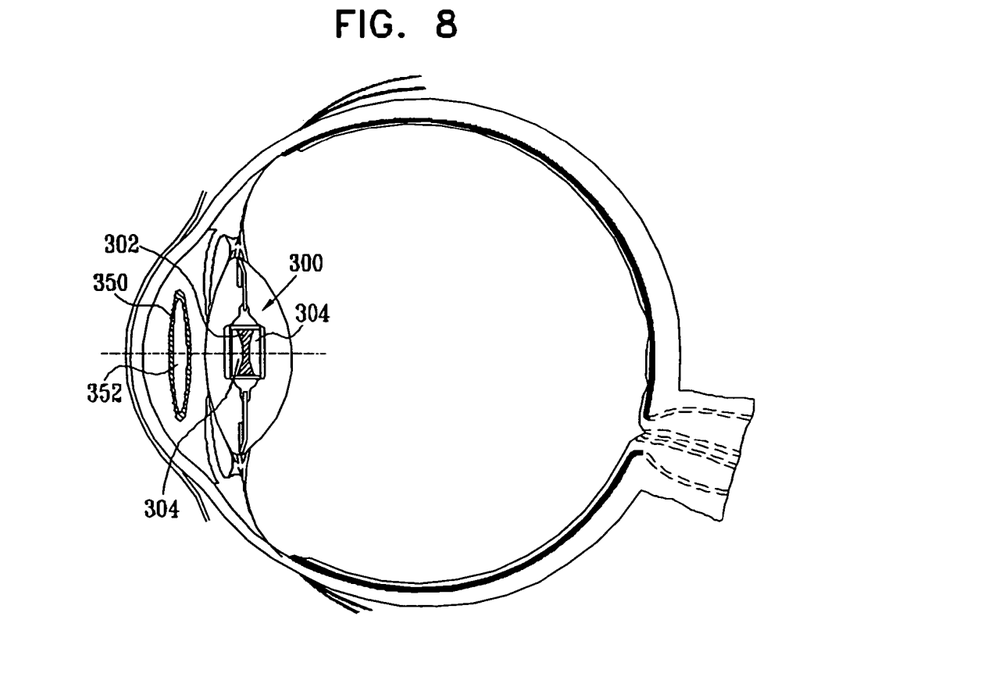
FIG. 8 is a simplified side view sectional illustration of an intraocular lens system of the type shown in FIGS. 7A-7G constructed and operative in accordance with a further embodiment of the present invention.

Reference is now made to FIG. 8, which is a simplified side view sectional illustration of an intraocular lens system of the type shown in FIGS. 7A-7G, constructed and operative in accordance with an additional embodiment of the present invention. In this embodiment, a positive lens 350 is located the anterior chamber of the eye. In the embodiment of FIG. 8, positive lens 350 includes an air capsule 352 to provide higher clarity focusing.

Figure 9A:
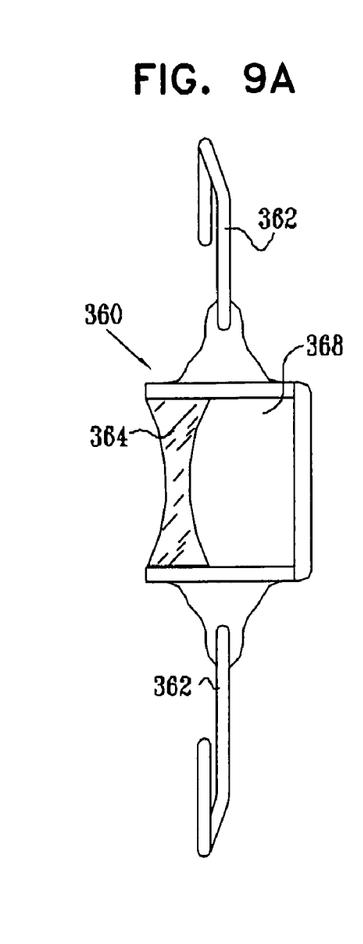
FIGS. 9A-9C are simplified side view illustrations of three examples of implanted sealed capsules of the type employed in the systems of FIGS. 7A-8.
Figure 9B:
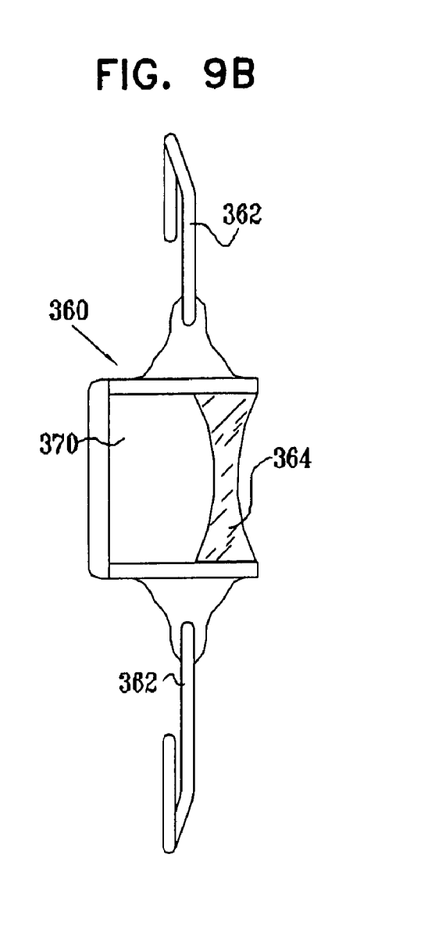
Figure 9C:
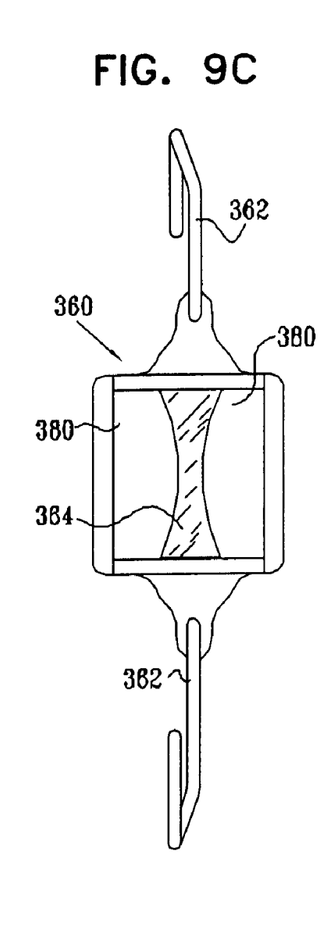

Reference is now made to FIGS. 9A-9C, which are simplified side view illustrations of three examples of implanted sealed capsules of the type employed in the systems of FIGS. 7A-8. It is seen that each of the capsules includes a sealed capsule body 360 and associated mounting haptics 362. Capsules of this type are described in applicants' U.S. patent application Ser. No. 09/678,559, filed Oct. 3, 2000 and entitled "TELESCOPIC INTRAOCULAR LENS", which is a divisional application of U.S. patent application Ser. No. 09/222,330, filed Dec. 29, 1998 and entitled "TELESCOPIC INTRAOCULAR LENS", subsequently abandoned, and U.S. patent application Ser. No. 09/721,916, filed Nov. 27, 2000 and entitled "TELESCOPIC INTRAOCULAR LENS", the disclosures of which are hereby incorporated by reference. Disposed within the capsule is a negative lens 364.

In the embodiment of FIG. 9A, a relatively large air bubble 368 is disposed rearward of negative lens 364.

In the embodiment of FIG. 9B, a relatively large air bubble 370 is disposed forward of negative lens 364.

In the embodiment of FIG. 9C, air bubbles 380 of approximately the same size are disposed forward and rearward of negative lens 364.

It will be appreciated by persons skilled in the art that the present invention is not limited to what has been particularly shown and described hereinabove. Rather the scope of the present invention includes both combinations and subcombinations of the various features described hereinabove as well as modifications and variations thereof as would occur to a person of skill in the art upon reading the foregoing specification and which are not in the prior art.

The invention claimed is:

1. An intraocular implant, for placement upstream of a retina for focusing objects at differing distances onto the retina, the intraocular implant comprising:
   a sealed capsule defining an optical path for light to pass therethrough, said sealed capsule including:
      an intraocular implant housing defining a capsule body; and
      a transparent front sealing plate and a transparent back sealing plate hermetically sealed to said capsule body;
   at least one first lens and at least one second lens enclosed in said sealed capsule;
   a variable positioner, enclosed in said sealed capsule, said variable positioner comprising:
      a variable displacer, operative to variably position at least one of said lenses along its optical axis relative to another at least one of said lenses, and to thereby focus objects located at multiple distances onto the retina; and
      a focus control assembly comprising circuitry, said focus control assembly being operative to provide variable positioning control input to said variable displacer; and
   mounting structure connected to said sealed capsule for mounting said implant in an eye.

2. An intraocular implant according to claim 1 and wherein said focus control assembly comprises a range finder.

3. An intraocular implant according to claim 1 and wherein said focus control assembly comprises a focus resolver.

4. An intraocular implant according to claim 1 and wherein said focus control assembly is responsive to a user input.

5. An intraocular implant according to claim 1 and wherein said variable displacer comprises:
   a mounting for at least one of said lenses;
   at least one magnet; and
   at least one electromagnetic coil, interacting with said at least one magnet.

6. An intraocular implant according to claim 1 and wherein said focus control assembly is responsive to an input from an input device external to said sealed capsule.

7. An intraocular implant according to claim 1 and wherein focusing objects at differing distances onto the retina is achieved using only said variable positioner.

8. An intraocular implant according to claim 5 and wherein said focus control assembly comprises a range finder.

9. An intraocular implant according to claim 5 and wherein said focus control assembly comprises a focus resolver.

* * * * *